(12) United States Patent
Jones et al.

(10) Patent No.: US 10,780,260 B2
(45) Date of Patent: *Sep. 22, 2020

(54) STERILE CONNECTION LUER ACCESS DEVICE

(71) Applicant: The Johns Hopkins University, Baltimore, MD (US)

(72) Inventors: Cameron C. Jones, Pikesville, MD (US); Clifford R. Weiss, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/738,432

(22) PCT Filed: Jun. 23, 2016

(86) PCT No.: PCT/US2016/039036
§ 371 (c)(1),
(2) Date: Dec. 20, 2017

(87) PCT Pub. No.: WO2016/210142
PCT Pub. Date: Dec. 29, 2016

(65) Prior Publication Data
US 2018/0185628 A1    Jul. 5, 2018

Related U.S. Application Data

(60) Provisional application No. 62/183,475, filed on Jun. 23, 2015.

(51) Int. Cl.
*A61M 39/14*    (2006.01)
*A61M 39/26*    (2006.01)
(Continued)

(52) U.S. Cl.
CPC ............ *A61M 39/14* (2013.01); *A61M 39/24* (2013.01); *A61M 39/26* (2013.01);
(Continued)

(58) Field of Classification Search
CPC ............ A61M 2039/261; A61M 39/26; A61M 2039/2433; A61M 2039/0036;
(Continued)

(56) References Cited

U.S. PATENT DOCUMENTS 4,610,469 A     9/1986  Wolff-Mooij
10,537,727 B2 *  1/2020  Jones .................... A61M 39/26
(Continued)

*Primary Examiner* — William R Carpenter
*Assistant Examiner* — Hamza A Darb
(74) *Attorney, Agent, or Firm* — Mintz Levin Cohn Ferris Glovsky and Popeo, P.C.; Peter F. Corless; Carolina E. Säve

(57) ABSTRACT

A luer access device (LAD) and a method of attaching the same are provided to create a sterile fluid-flow path. The LAD includes a female luer connector that has an internal female split septum disposed at a proximal end thereof and is coupled to an internal surface of the LAD. A male luer connector is coupled to an external surface of the female split septum. Additionally, a male split septum is disposed within a male luer tip and seals an opening of a distal end of the male luer connector. At least one aperture is disposed through a sidewall of the distal end of the male luer connector. An internal cannula is exposed out of the female luer connector to open the female split septum upon engagement with the male luer connector.

27 Claims, 15 Drawing Sheets

(51) Int. Cl.
*A61M 39/24* (2006.01)
*A61M 39/10* (2006.01)

(52) U.S. Cl.
CPC .............. *A61M 2039/1033* (2013.01); *A61M 2039/1072* (2013.01); *A61M 2039/1083* (2013.01); *A61M 2039/1088* (2013.01); *A61M 2039/2426* (2013.01); *A61M 2039/2433* (2013.01); *A61M 2039/261* (2013.01); *A61M 2039/263* (2013.01)

(58) Field of Classification Search
CPC ............ A61M 39/14; A61M 2039/263; A61M 2039/2426; A61M 39/24; A61M 2039/1033; A61M 2039/1088; A61M 2039/1083; A61M 39/10; A61M 39/18
See application file for complete search history.

(56) References Cited

U.S. PATENT DOCUMENTS

| | | | |
|---|---|---|---|
| 2006/0264849 A1 | 11/2006 | Lopez et al. | |
| 2008/0172003 A1* | 7/2008 | Plishka | A61M 39/045 604/249 |
| 2010/0030163 A1 | 2/2010 | Carrez et al. | |
| 2013/0085473 A1* | 4/2013 | Weilbacher | A61M 39/00 604/513 |
| 2014/0031765 A1 | 1/2014 | Siopes et al. | |
| 2014/0249487 A1* | 9/2014 | Lynn | A61M 39/10 604/256 |

\* cited by examiner

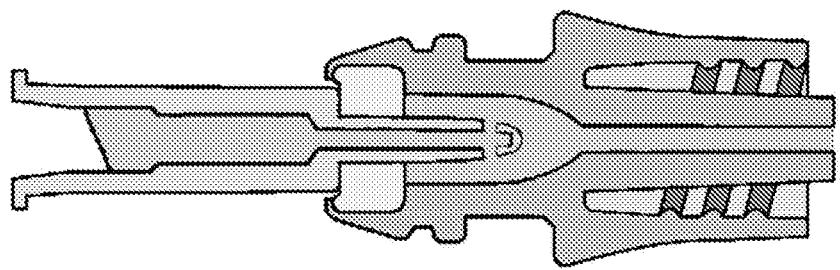
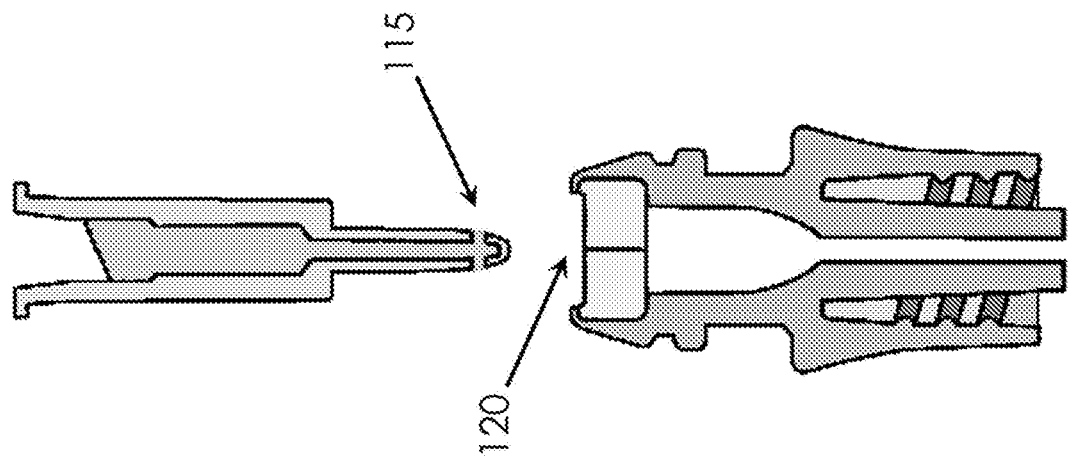
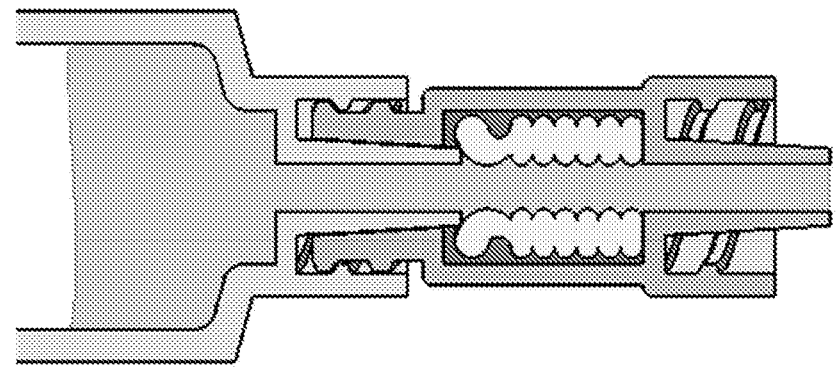
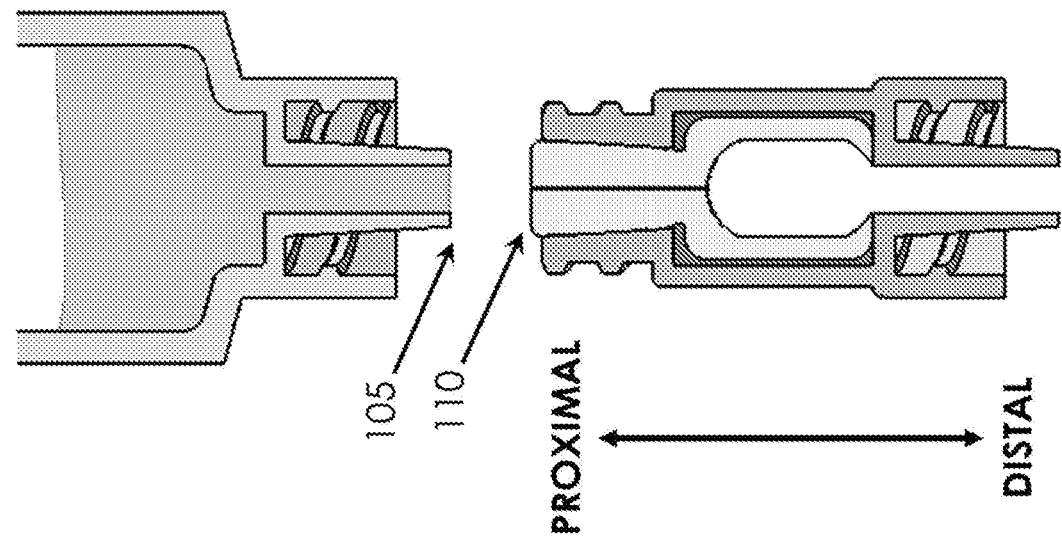

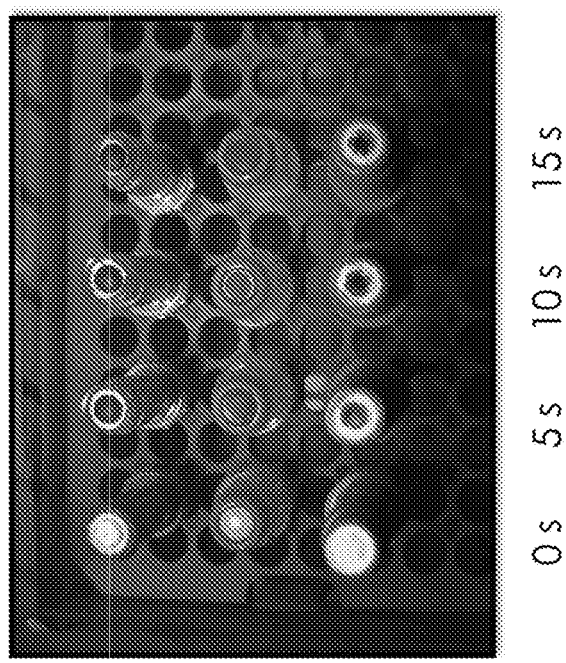

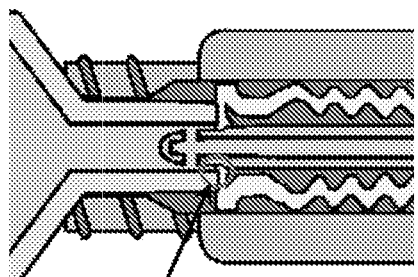
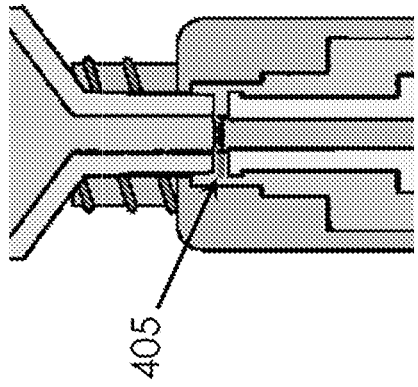
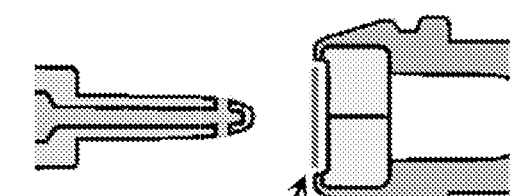
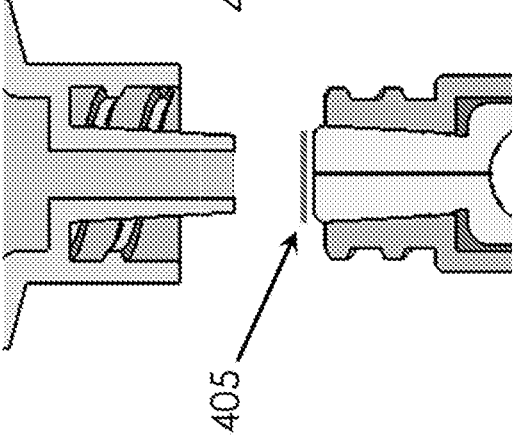
FIG. 4A RELATED ART
FIG. 4B RELATED ART
FIG. 4C RELATED ART
FIG. 4D RELATED ART

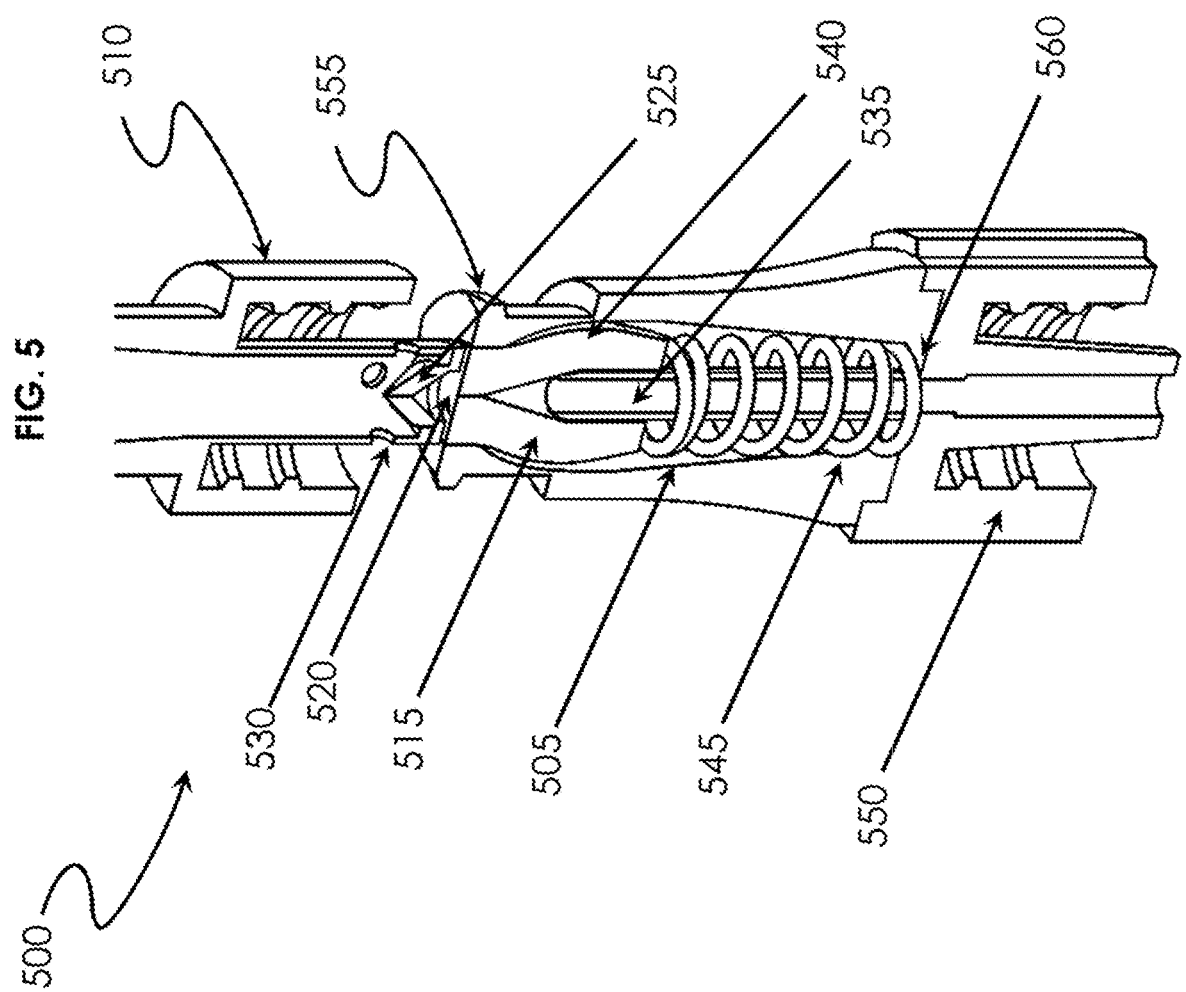

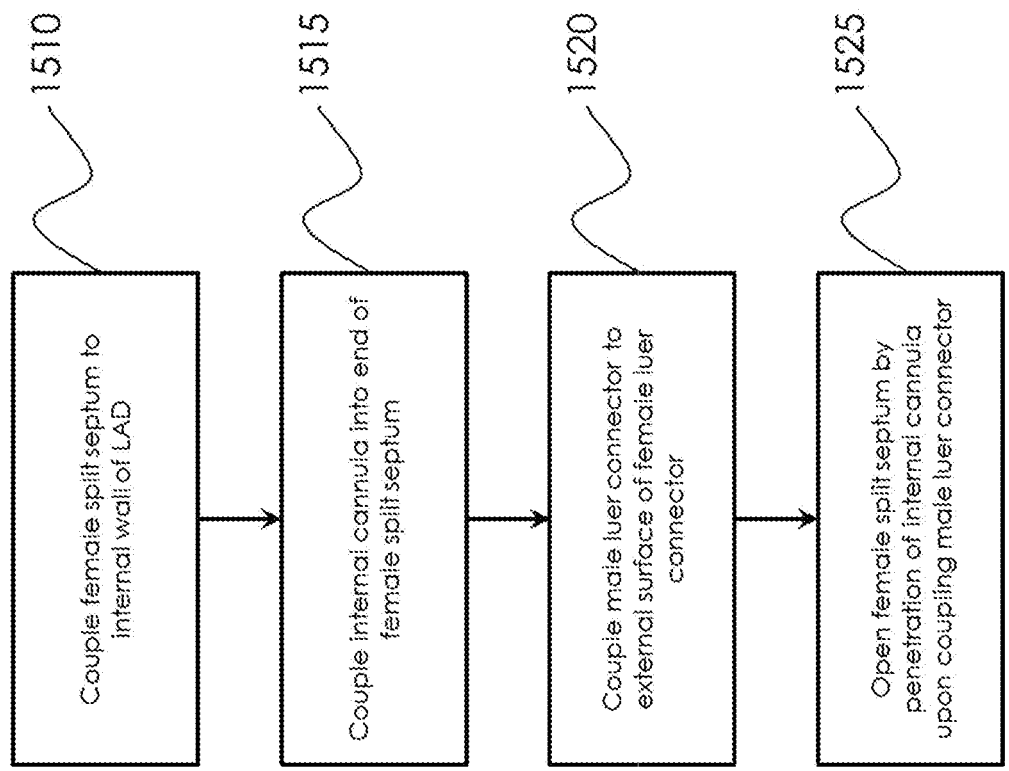

STERILE CONNECTION LUER ACCESS DEVICE

CROSS REFERENCE TO RELATED APPLICATIONS

The present application claims priority from U.S. provisional application No. 62/183,475 filed Jun. 23, 2015, which is incorporated herein by reference in their entirety.

FIELD OF INVENTION

The present invention relates to a luer access device, and more particularly, relates to a sterile connection luer access device that provides a sterile connection preventing egress of contamination into an indwelling vascular access line.

BACKGROUND

Needleless connectors are commonly used in the medical field during administration of fluids to provide life-sustaining support to patients. Disposable needleless connectors may be attached to the proximal end of an indwelling vascular catheter or to other ports used for administering fluids. Such devices were originally developed to prevent commonly occurring needle-stick injuries to healthcare providers.

FIGS. 1A-1D show various types of needle-free connectors according to the related art. In particular, FIGS. 1A-1D illustrate the mechanism by which different types of needleless connectors function, which consist of a male connector and a female connector, and a re-sealable septum disposed within the female connector (typically, the female connector is referred to, in its entirety, as the needleless connector). FIGS. 1A and 1B show a luer access device (LAD), wherein a male luer tip 105 depresses a re-sealable split septum within the female luer tip 110 to provide fluid communication. FIGS. 1C and 1D show the male connector as a blunt-tip cannula 115 used to access a split septum 120.

FIGS. 2A-2C show various types of female needleless connectors of the related art. In particular, FIG. 2A shows a connector with a single septum that is displaced upon attachment of the male connector. The female connector contains no internal features apart from the re-sealable septum. One disadvantage of this type of connector is the large negative fluid displacement upon withdrawal of the male connector, which may result in fluid reflux in the proximal catheter tip. FIG. 2B shows a type of connector that includes an internal actuator to achieve positive fluid displacement upon detachment of the male component. The positive fluid displacement causes the fluid to flow between the outer housing and the internal actuator component and results in a small release of fluid through the distal tip. FIG. 2C shows a female connector containing an internal blunt-tip cannula which pierces the septum as it is displaced within the device upon attachment of the male connector. Fluid administration through the female connector occurs through the blunt tip cannula. This design results in a neutral fluid displacement as the withdrawal of the male connector causes the septum to re-seat around the internal cannula with minimal fluid displacement (usually less than ±10 microliters).

However, since the proximal surface of the septum on the female components shown in FIGS. 1A-1D and FIGS. 2A-2C is exposed to the environment, it must be disinfected prior to attachment of the male connector. However, incomplete disinfection may result in an increased risk of device contamination and a bloodstream infection due to the egress of microorganisms on exposed contact surfaces. FIG. 3 shows a simulated disinfection protocol for various needleless connectors of the related art, Type A, Type B, and Type C, and which shows the surface following disinfection protocols of 0, 5, 10, and 15 seconds. As seen from FIG. 3, all of the devices show areas of residual contamination. Such contamination may be caused by different variants such as design of the connector, use of the system, as well as frequency of changing connectors.

FIGS. 4A-4D show the susceptibility of needleless connectors to contamination when an external surface is not properly disinfected. For example, the male tip of a sterile connecting medical component (e.g., a syringe or other similar article) may become contaminated when a pathogen 405 remains on the external septum surface, as shown in FIGS. 4A and 4B. In these configurations, the male connector and/or the fluid to be administered within the attaching article may become contaminated during the depressing or piercing of the female septum. Additionally, systems that incorporate internal features such as those shown in FIGS. 4C and 4D may become contaminated when the outer surface of the septum contacts the internal features. Attempts to disinfect the internal features of the needleless connector may be unsuccessful due to the inaccessibility of the contaminated surface and therefore create a potential risk to the patient if the contamination proliferates and is flushed into the bloodstream.

As shown by the discussion of the related art above, although the currently available needleless connectors have been developed to reduce the risk of needle-stick injuries, these current designs may also be associated with an increased risk of catheter-related bloodstream infections. Accordingly, it would be advantageous to provide a needleless connector that is capable of providing a sterile connection to administer fluids to patients by preventing exposed surfaces on the female needleless connector from contaminating both the attaching male article and internal surfaces which are part of the fluid flow pathway.

SUMMARY

The present invention provides a needleless access device that achieves a sterile connection between male and female connectors to thus reduce potential catheter-related bloodstream infections.

According to one aspect of the present invention, a luer access device (LAD) is provided that comprises a female luer connector that has an internal female split septum disposed at a proximal end thereof and is coupled to an internal surface of the LAD. In addition, a male luer connector is coupled to an external surface of the female split septum. A male split septum is disposed within a male luer tip and seals an opening of a distal end of the male luer connector. At least one aperture is disposed through a sidewall of the distal end of the male luer connector. Further, an internal cannula may be exposed out of the female luer connector to open the female split septum upon engagement with the male luer connector. The male split septum may also seal an opening of the aperture by the penetration of the internal cannula.

In an additional aspect, the male split septum may seal an opening of the aperture when the female split septum is opened to provide fluid communication between the male luer connector and the female luer connector. Particularly, the female split septum may move down along the internal cannula upon engagement with the male luer connector to expose the internal cannula. The female split septum may be moved in response to an elastic force output by a resilient member disposed between the female split septum and a bottom of the LAD. The resilient member may be a spring or an elastomeric polymer that undergoes elastic deformation upon engagement with the male luer connector.

In another aspect, an interior of the male luer connector may be threaded to engage with an external wall of the female luer connector. The distal end of the male luer connector may also include a plurality of apertures. Alternatively, the plurality of apertures may be formed as slots.

In yet another aspect, the male split septum may be formed as a valve. In particular, a distal end of an inner conduit of the male luer connector may form a seal against a proximal surface of the valve.

According to another aspect of the present invention, a method is provided for coupling a luer access device. The method may include sealing a distal end of a male luer connector using a male split septum and coupling the male luer connector to an external surface of an internal female split septum that is disposed at a proximal end of a female luer connector. An internal cannula disposed in a passageway of the female luer connector penetrates through the female split septum to open the female split septum. Additionally, an opening of at least one aperture is sealed using the male split septum as the internal cannula penetrates through the opened female split septum and the male split septum. The aperture is particularly disposed through a sidewall of the distal end of the male luer connector.

In a further aspect, the female split septum may be coupled to an internal wall of the LAD and the female split septum deforms during the opening thereof to prevent an outer surface from contacting the internal cannula. The female split septum may be moved down the internal cannula in response to an elastic force output by a resilient member disposed between the female split septum and a bottom of the LAD. The resilient member may be a spring or an elastomeric polymer that undergoes elastic deformation upon coupling of the female luer connector and the male luer connector.

According to yet another aspect of the present invention, a method is provided for coupling a luer access device that includes coupling a female split septum to an internal wall of the LAD and coupling an internal cannula into an end of the female split septum within a passageway of the female luer connector. A male luer connector is coupled to an external surface of the female luer connector and the female split septum is opened by penetration of the internal cannula upon coupling with the male luer connector. Further, the female split septum deforms during the opening thereof to prevent an outer surface from contacting the internal cannula. When the female split septum is opened, the internal cannula penetrates into the male luer connector to couple the male luer connector and the female luer connector and provide a fluid communication there between.

Notably, the present invention is not limited to the combination of the luer access device elements as listed above and may be assembled in any combination of the elements as described herein.

Other aspects of the invention are disclosed infra.

BRIEF DESCRIPTION OF THE DRAWINGS

The embodiments herein may be better understood by referring to the following descriptions in conjunction with the accompanying drawings in which like reference numerals indicate identically or functionally similar elements, of which:

FIGS. 1A-1D are views of needleless connectors including luer activated devices and blunt-tip cannulas according to the related art;

FIG. 3 shows results of a simulated disinfection protocol of needleless connector devices according to the related art;

FIGS. 4A-4D are views of needleless connector susceptibility according to the related art;

FIG. 5 is a view of a luer access device according to an exemplary embodiment of the present invention;

FIG. 15 is another flowchart showing the method of coupling a luer access device according to an exemplary embodiment of the present invention.

DETAILED DESCRIPTION

Figure 2C:
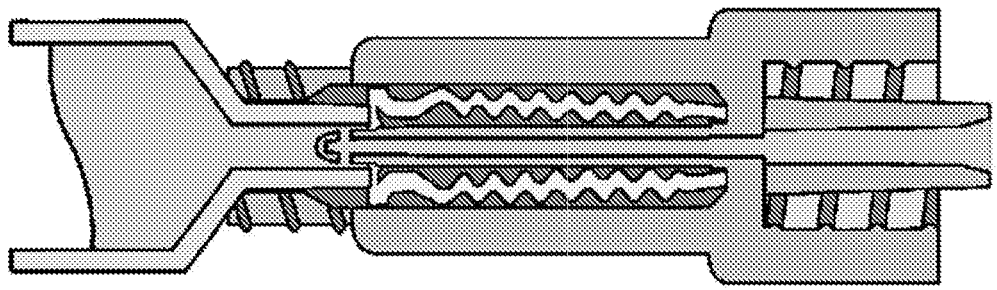
FIGS. 2A-2C are views of split-septum type luer access devices according to the related art.
Figure 2B:
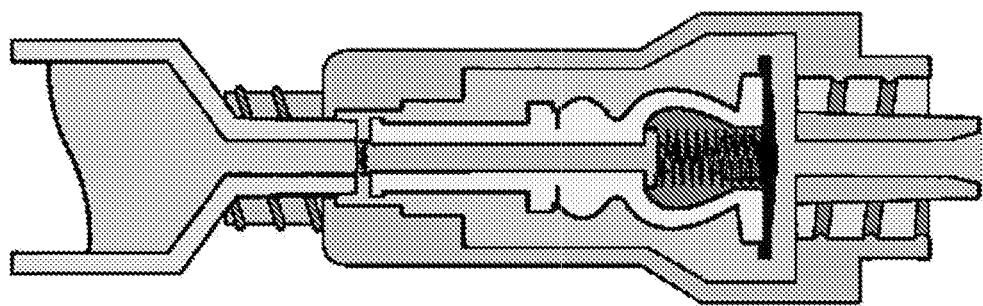
Figure 2A:
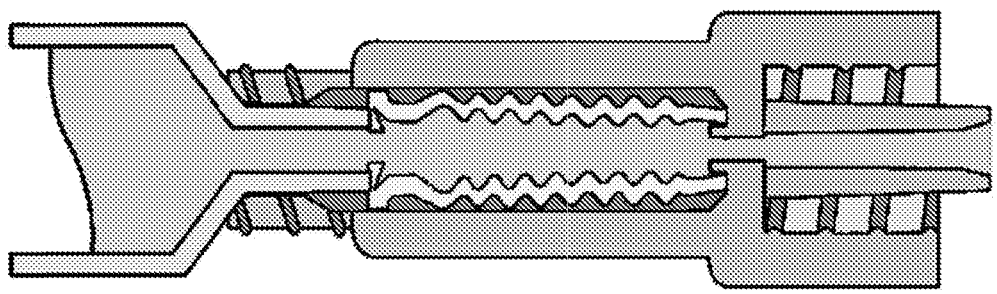

The presently disclosed subject matter will be described more fully hereinafter with reference to the accompanying drawings, in which some, but not all embodiments of the inventions are shown. Like reference numerals refer to like elements throughout. The presently disclosed subject matter may be embodied in many different forms and should not be construed as limited to the embodiments set forth herein; rather these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

In one aspect, the present invention is directed to a luer access device (LAD) having a split septum to provide a sterile connection between the luer connectors of the device. In particular, the present invention is directed to an LAD that facilitates a connection with medical articles and reduces the risk of catheter-related bloodstream infections by preventing the egress of bacterial contamination through the LAD. The split septum of the LAD in the present invention is opened and specifically deformed to provide fluid communication between the two connectors while preventing external contaminations from being in direct contact with the fluid or internal surfaces consisting of the fluid lumen. The prevention of the contamination contact with the fluid means that even during the attachment of the connectors, each surface remains sterile, unlike the related art in which external surfaces are disinfected prior to connection of a sterile medical device but are in contact with the fluid upon connection, thus increasing the susceptibility of contamination of the needleless connector and administration fluid.

FIG. 5 illustrates a partial sectional view of a needleless access system according to an exemplary embodiment of the present invention. As illustrated in FIG. 5, the access system 500 may include a female luer connector 555 and a male luer connector 510. In particular, the female luer connector 555 may include a female split septum 515 having an external surface 520, and an internal cannula 535. The male luer connector 510 may include a male split septum 525 and at least one aperture 530. The connection of these components will be described in further detail herein below.

As illustrated in FIG. 5, the internal female split septum 515 may be disposed at a proximal end of the female luer connector 555 and may be coupled to an internal surface of the LAD 505 having a particular geometric shape (i.e., predefined geometry). The female split septum 515 may be designed to have a predefined geometry 540 capable of deforming in a prescribed manor while being opened. Further, the male luer connector 510 may be coupled to an external surface 520 of the female split septum 515. The male split septum 525 may be disposed within a male luer tip (e.g., at the tip of the male luer connector) to seal an opening of the distal end of the male luer connector 510. The male luer connector 510 may also include at least one aperture 530 that is disposed through a sidewall of a distal end of the male luer connector 510 to enable priming (i.e., to fill with fluid) of the connecting medical article prior to coupling with the female luer connector 555.

Figure 6C:
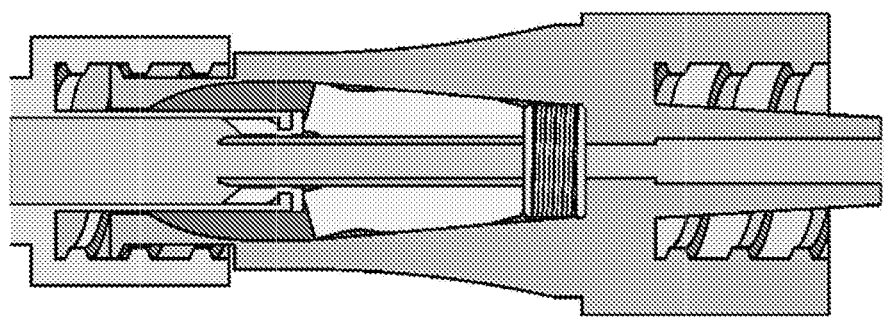
FIGS. 6A-6C are views of engaging a male luer connector and a female luer connector according to an exemplary embodiment of the present invention.
Figure 6B:
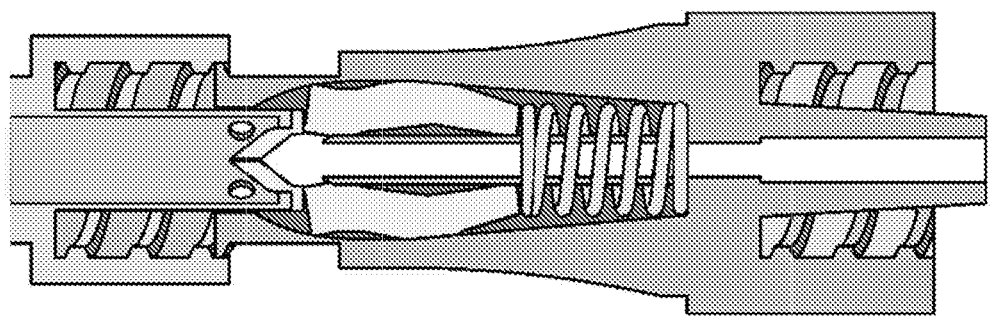
Figure 6A:
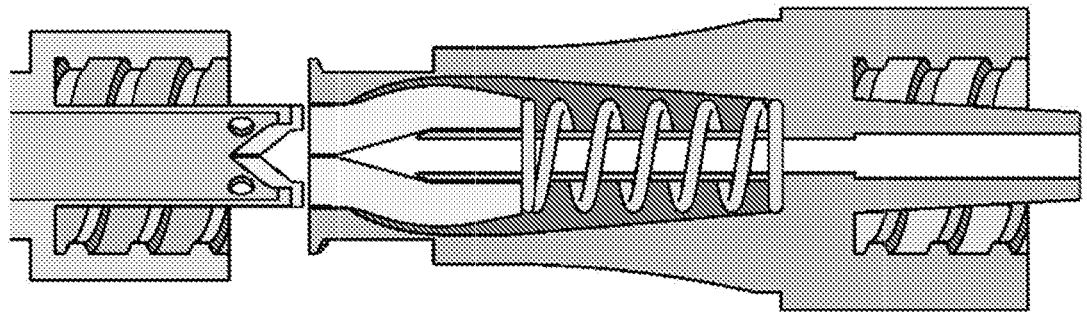

Furthermore, with respect to FIGS. 6A-6C, which illustrate views of engaging the female luer connector and the male luer connector, the internal cannula 535 may be exposed out of the female luer connector 555 to open the female split septum 515 upon engagement with the male luer connector 510. Specifically, as seen in FIG. 6A, the LAD is sealed by the female split septum 515 and the internal cannula 535 is coupled into an end of the female split septum 515 within a passageway of the female luer connector 555. In addition, in FIG. 6A the male luer connector may be primed but remains sealed in the axial direction.

Then, as shown in FIG. 6B, the internal cannula 535 begins to penetrate through the female split septum 515 to open and partially displace the female split septum 515. The female split septum 515 may be specifically deformed due to the internal geometries of the LAD (see 505, 535, and 540). As the cannula 535 penetrates through the female split septum 515, the male luer connector 510 engages with the female luer connector 555, thus causing a resilient member 545 to deform. Although in FIG. 6B the male luer connector 510 is engaged with the female luer connector 555, the male luer connector 510 remains disengaged from the internal cannula 535 and thus remains sealed in the axial direction. Further, FIG. 6B shows the female split septum 515 is moved down along the internal cannula 535 upon engagement with the male luer connector 510 to expose the internal cannula 535. The female split septum 515 is thus moved in response to the elastic force which may be output by the resilient member 545 disposed between the female split septum 515 and a bottom of the LAD 560. In one embodiment, the resilient member 545 may be a spring or an elastomeric polymer that undergoes elastic deformation upon engagement with the male luer connector 510.

Referring now to FIG. 6C, illustrating the complete engagement of the male and female luer connectors (i.e., the male luer connector is seated against the female luer connector), the internal cannula 535 penetrates through the male split septum 525 and into the male luer connector 510 to provide a direct fluid-flow path between the male and female luer connectors. As also seen in FIG. 6C, the complete engagement of the luer connectors results in a further compression of the resilient member 545. Additionally, an interior of the male luer connector 510 may be threaded to engage with the external wall of the female luer connector 555 upon the complete engagement of the luer connectors. As will be described in further detail with reference to FIG. 9, once the internal cannula 535 has penetrated into the male luer connector 510, the male split septum 525 seals an opening of the aperture 530 to prevent an external surface 520 of the female split septum 515 from contacting the sterile surfaces of the male luer connector and the fluid prime (see FIGS. 6A and 6B), thus providing the sterile connection between the luer connectors and a sterile fluid-flow path. Notably, the present invention is not limited to merely one aperture but a plurality of apertures may be disposed through the sidewall of the male luer connector.

Figure 7:
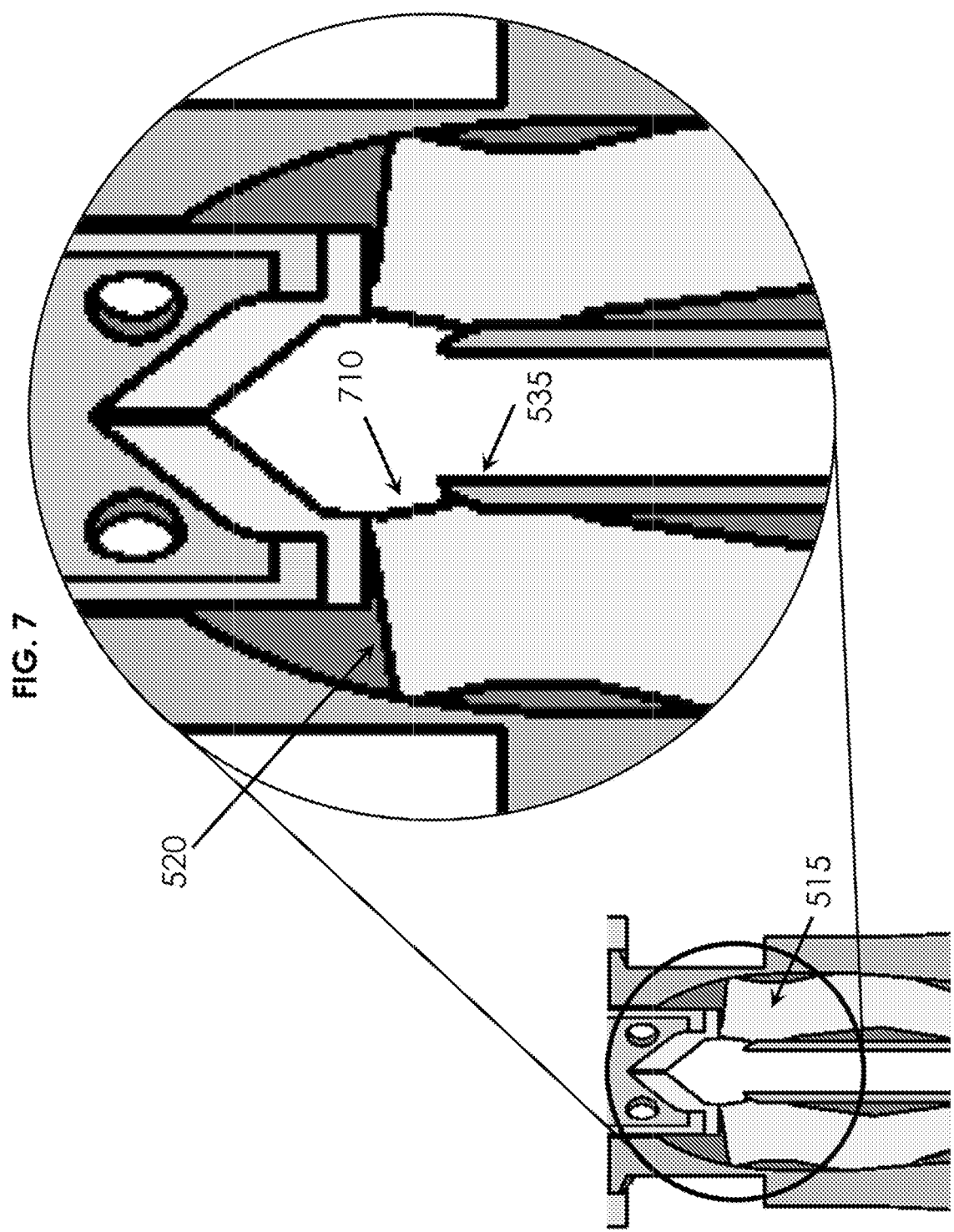
FIG. 7 is a detailed view of a female split septum in an opened state according to an exemplary embodiment of the present invention.

FIG. 7 illustrates a detailed view of female split septum in an opened state according to an exemplary embodiment of the present invention. In particular, FIG. 7 shows that the particular geometrical shape 540 of the female split septum 515 and the internal LAD surface 505 prevent the external surface 520 thereof from contacting the internal cannula 535. Thus, any potential pathogen remaining on the external surface 520 of the female split septum 515 does not come in contact with (i.e., does not touch) the internal cannula 535. Instead, portion 710 of female split septum 515 contacts the internal cannula 535 and remains a sterile internal surface. In other words, as seen in FIG. 7, only an internal portion 710 of the female split septum 515 contacts the internal cannula 535 while an external surface 520 of the female split septum 515 is pushed outward due to the deformation of the female split septum 515. Notably, the present invention is not limited to the particular geometric deformation as shown in FIG. 7. Any geometric deformation may be used as long as an external surface of the split septum does not contact the internal cannula, thus preventing any potential contamination into the fluid-flow path.

Figure 8C:
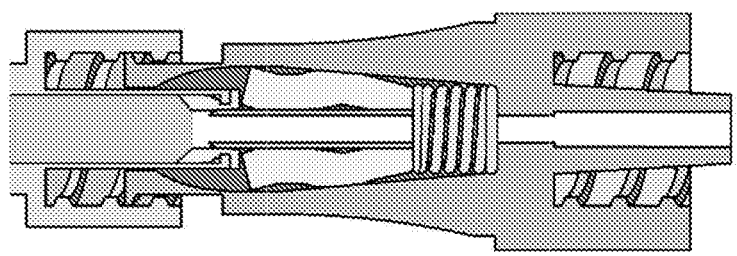
FIGS. 8A-8C are views of the opening of a male split septum according to an exemplary embodiment of the present invention.
Figure 8B:
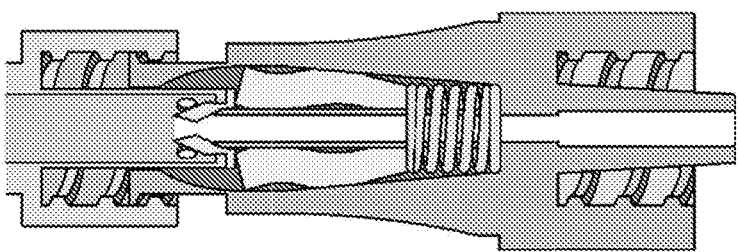
Figure 8A:
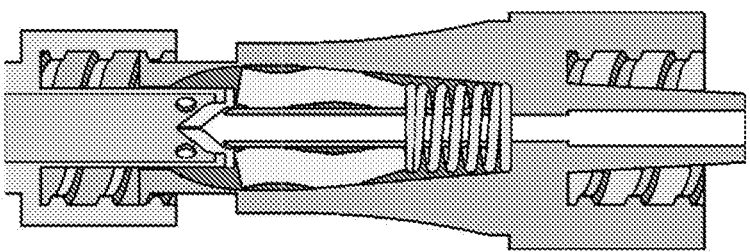

Moreover, FIGS. 8A-8C illustrate views of the opening of the male split septum according to an exemplary embodiment of the present invention. As seen in FIG. 8A, the female split septum 515 has been displaced and opened by the penetration of the internal cannula 535 and the male split septum 525 remains a seal to the distal opening of the male luer connector 510 (i.e., remains in a closed state). Then, as seen in FIG. 8B, the internal cannula 535 penetrates into the male luer connector 510, partially pushing through the male split septum 525, thus causing the resilient member 545 to partially compress. In FIG. 8B, the internal cannula 535 has not fully penetrated through the male split septum 525 and the aperture 530 remains exposed.

In particular, FIG. 8B shows that the resilient member 545 is further compressed as the male luer connector 510 begins to advance towards the female luer connector 555, that is, begins to further engage with the female luer connector 555. As the male luer connector 510 engages with the female luer connector 555, the external wall of the female luer connector 555, further engages with the threaded interior of the male luer connector 510. Additionally, FIG. 8C illustrates the complete opening of the male split septum 525 by the penetration of the internal cannula 535 to connect the female and male luer connectors. Upon such penetration, the male split septum 525 seals the opening of the aperture 530 disposed at the male luer tip of the male luer connector 510.

Figure 9:
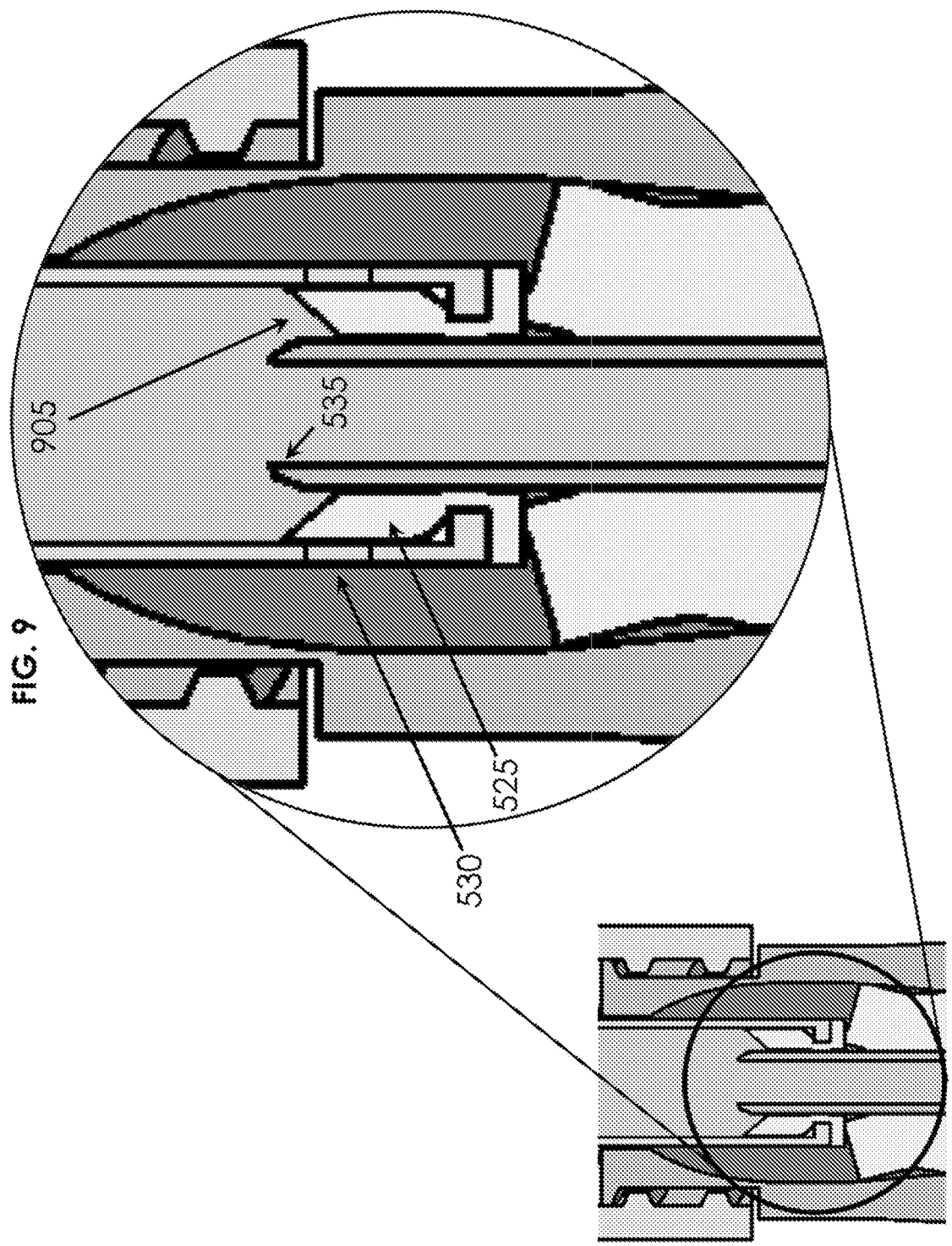
FIG. 9 is a detailed view of a male split septum in an opened configuration according to an exemplary embodiment of the present invention.

In further detail, FIG. 9 illustrates a detailed view of FIG. 8C, in which the male split septum is in an opened configuration according to an exemplary embodiment of the present invention. As shown in FIG. 9, in the final stage of the connection process, the male luer connector 510 is fully opened by the penetration of the internal cannula 535, that is, the male luer connector 510 is seated against the female luer connector 555 to provide a sterile-to-sterile fluid connection there between. Particularly, the male split septum 525 is opened to thus seal the aperture(s) 530 disposed through the wall of the male luer connector 510. The fluid-side surface 905 of the male split septum 525 is a sterile surface that remains sterile since the internal cannula 535 has not been in contact with any contaminated surfaces while penetrating through the female split septum 515 into the male luer connector 510. Accordingly, the LAD of the claimed invention is capable of providing a fluid-flow path of sterile surfaces.

Figure 10:
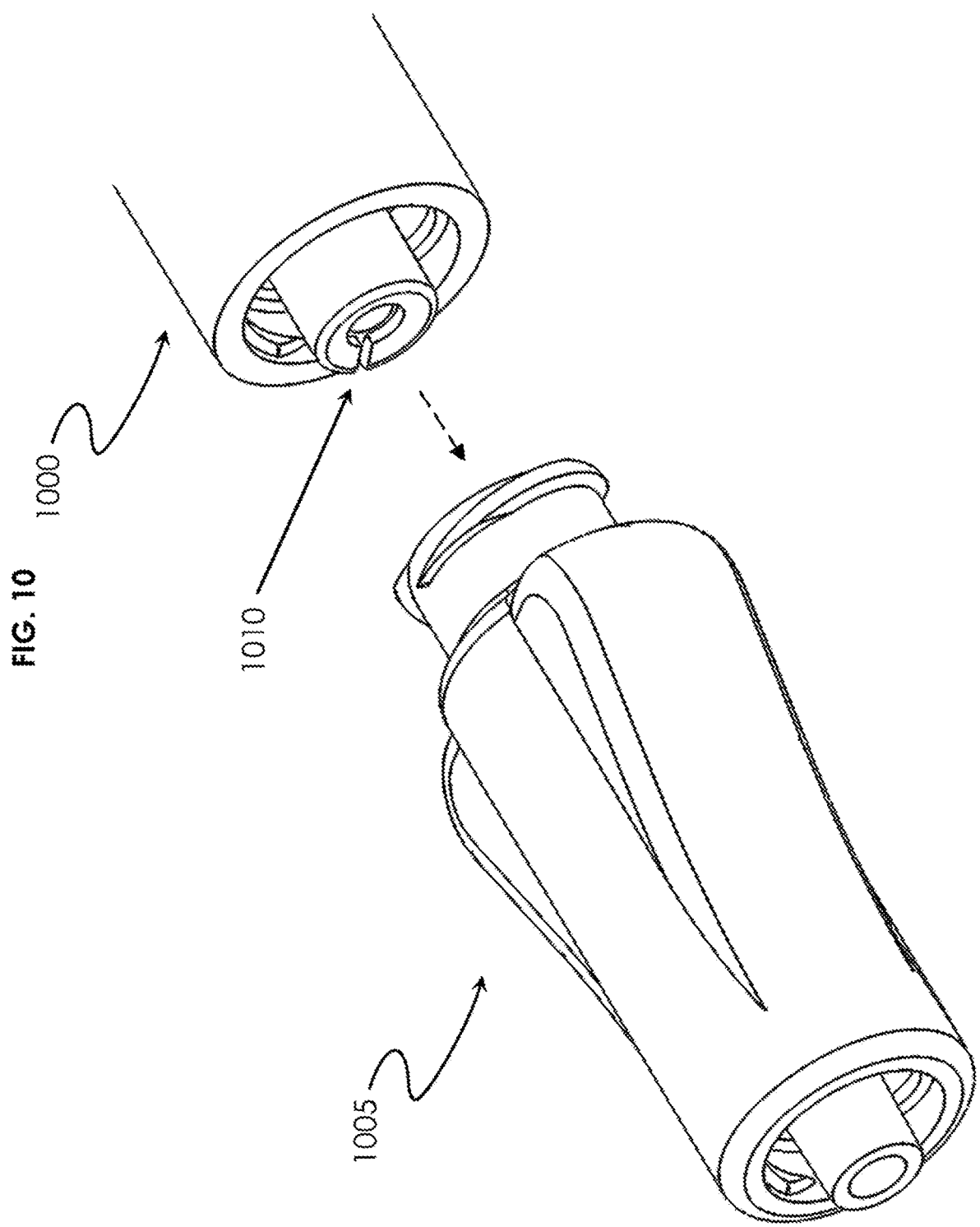
FIG. 10 is a view of a luer access device according to another exemplary embodiment of the present invention.

FIG. 10 illustrates a perspective view of a needle-free (e.g., needleless) access system according to an exemplary embodiment of the present invention. The access system in FIG. 10 may include a male luer connector 1000 and a female luer connector 1005. In particular, the male luer connector 1000 may include at least one slot formed in the side housing 1010 and extending to the distal tip for exhaust during device priming. This feature will be described in further detail herein below.

Figure 11:
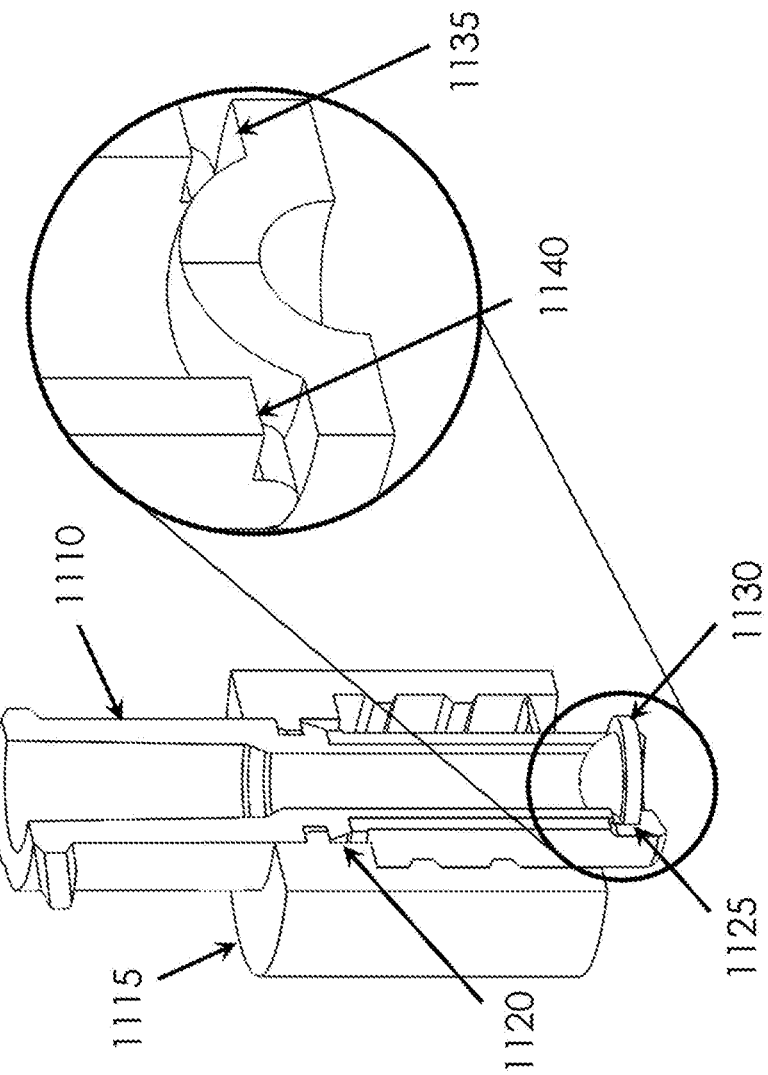
FIGS. 11A-11C are detailed views of a male luer connector according to another exemplary embodiment of the present invention.

FIGS. 11A-11C illustrate a series of perspective and sectional views of a male luer connector according to an exemplary embodiment of the present invention. The male luer connector 1100 in FIG. 11A is depicted as an adapter with male and female receiving ends for adapting current medical articles for use with the sterile needle-free access system. However, the proximal end of the assembly 1100 may be molded in one process with syringes, infusion sets, or similar medical articles.

In particular, as shown in FIG. 11A, the distal tip of the male luer connector 1100 may include one or more slots 1105 extending from the distal tip of the male luer connector.

FIG. 11B shows a partial cross-sectional view of the male luer connector from FIG. 11A. The figure illustrates a preferred assembly of three components: an inner connector and conduit 1110, an outer jacket 1115, and a valve 1130. The dome valve 1130 of FIG. 11B is shown without invoking the cross-section applied to the inner conduit 1110 and outer jacket 1115 to illustrate the full profile of the member. In the assembly shown in FIG. 11B, the inner conduit 1110 may slide into the outer jacket 1115 and may be joined by a locking mechanism 1120. The valve 1130 may be held between the inner conduit 1110 and the outer jacket 1115. The cross-sectional view of FIG. 11B illustrates that slot 1105 in FIG. 11A is formed in the outer jacket 1115 and overlaps with an opening in the distal tip of the inner conduit 1125.

FIG. 11C shows a magnification or detailed view of select features of the distal portion of the male luer connector in FIG. 11B. For clarity, the outer jacket 1115 is not illustrated in the magnification, and the cross-section of the dome valve 1130 is shown. In a preferred embodiment of the present invention, the distal end of the inner conduit may form a seal against the proximal surface 1135 of the valve 1130 with the exception of one or more notches 1140. The overlapping region 1125 between the slot 1105 and notch 1140 permits side-exhaust of the infusion prime since the one-way valve 1130 in its closed configuration prevents fluid flow in the axial direction.

Figure 12:
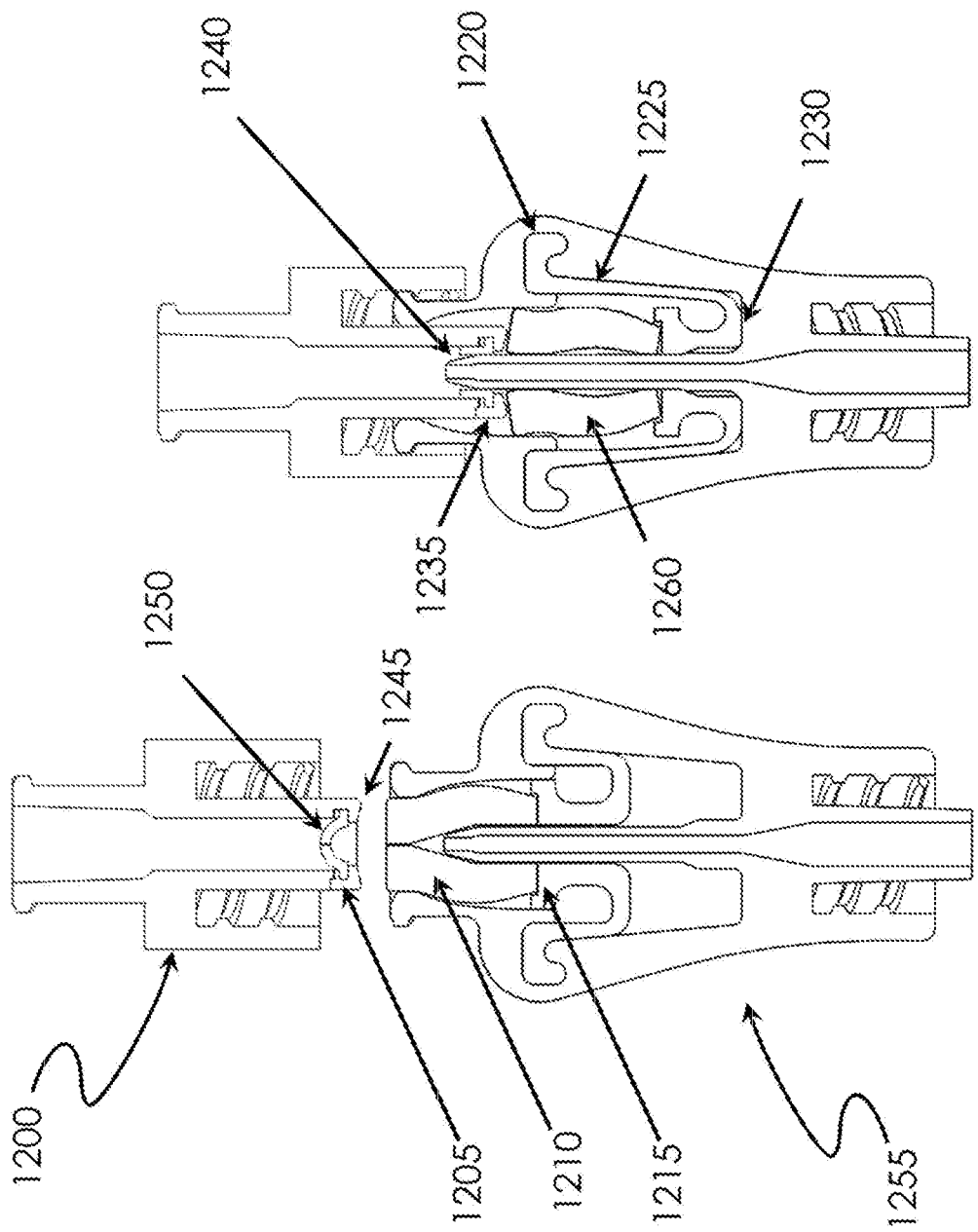
FIGS. 12A-12B are views of engaging male luer connector and a female luer connector according to another exemplary embodiment of the present invention.

Referring now to FIGS. 12A and 12B, the figures illustrate the internal features of a needle-free access system according to an exemplary embodiment of the present invention. As previously noted, the illustration of the male luer connector 1200 as an adapter is not intended to limit the proximal design or coupling with medical articles common to the art. Particularly, as illustrated in FIG. 12A, the male luer connector 1200 may include a valve 1250 and side slot 1205. The female luer connector 1255 may include a split septum 1210 and a resilient member 1215. FIG. 12A illustrates the male luer connector 1200 prior to engaging with the female connector 1255.

FIG. 12B illustrates the male luer connector 1200 of FIG. 12A fully engaged with the female luer connector 1255 of FIG. 12A. The figure shows that upon engagement of the two members, the female septum 1260 has undergone a preferential deformation as shown in previous illustrations (e.g., FIG. 7). Likewise, the valve 1250 has been opened by an internal cannula 1240 which seals the slot 1235 on the male luer connector. The figure further illustrates the resilient member 1215 has been elastically elongated 1225 along the axial direction towards the LAD bottom 1230. Having been maintained by tabbed features 1220 within the housing of the female luer connector 1255, the resilient member 1215 may return to a resting position (e.g., an original position) as shown in FIG. 12A, thereby resetting the female septum to a closed state 1210.

Figure 13:
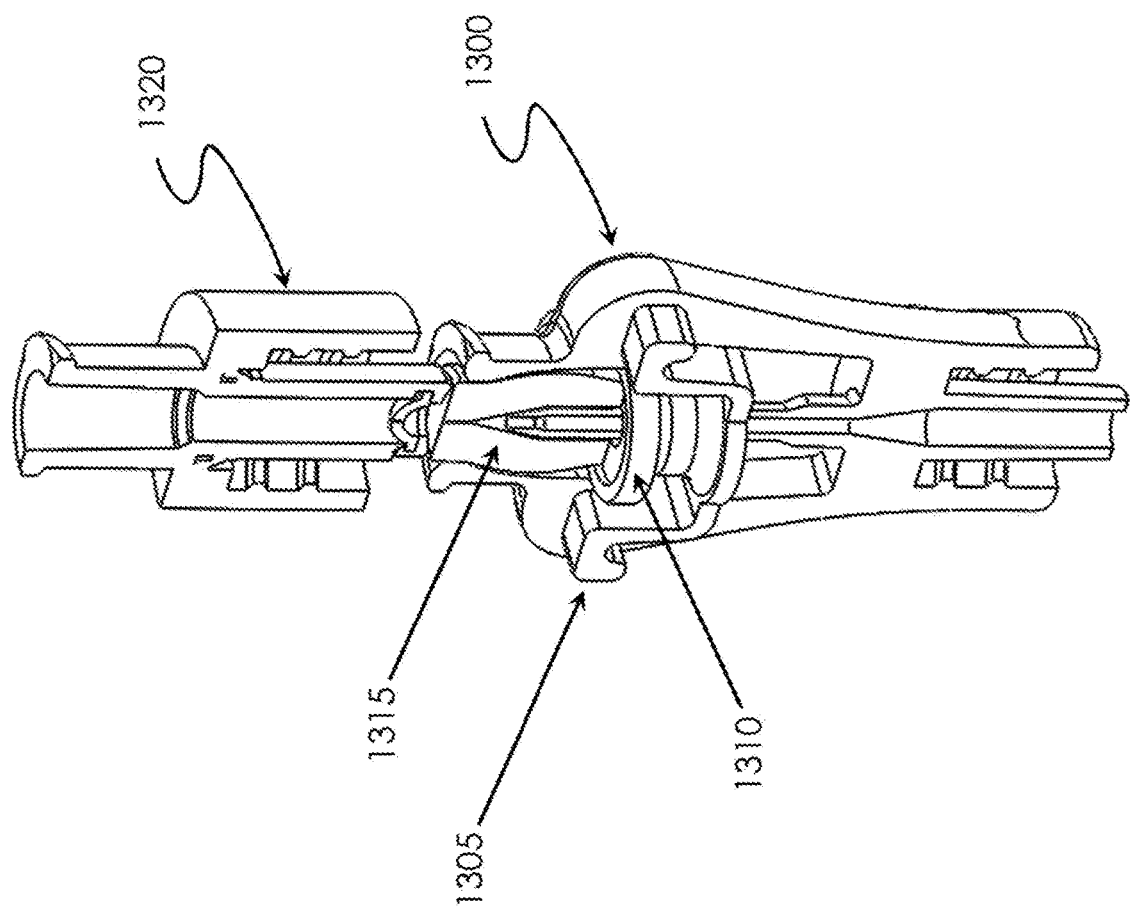
FIG. 13 is a view of a luer access device according to another exemplary embodiment of the present invention.

FIG. 13 illustrates the design of a proposed resilient member in a perspective partial cross-sectional view of the luer access system according to a preferred embodiment. The female connector 1300 is shown in a resting (not connected) state. The resilient member may include a region 1305 affixed within a matching or corresponding shaped section of the housing of the female connector 1300, which provides a method for returning the elongated elastic member back to the resting shape. Furthermore, the resilient member may include a region 1310 that shares a common surface with the female split septum 1315 that, upon deformation of the female split septum following engagement between the attaching male luer connector, creates a force to return the female septum 1315 back to the resting (closed) state when the male luer connector 1320 is detached.

Figure 14:
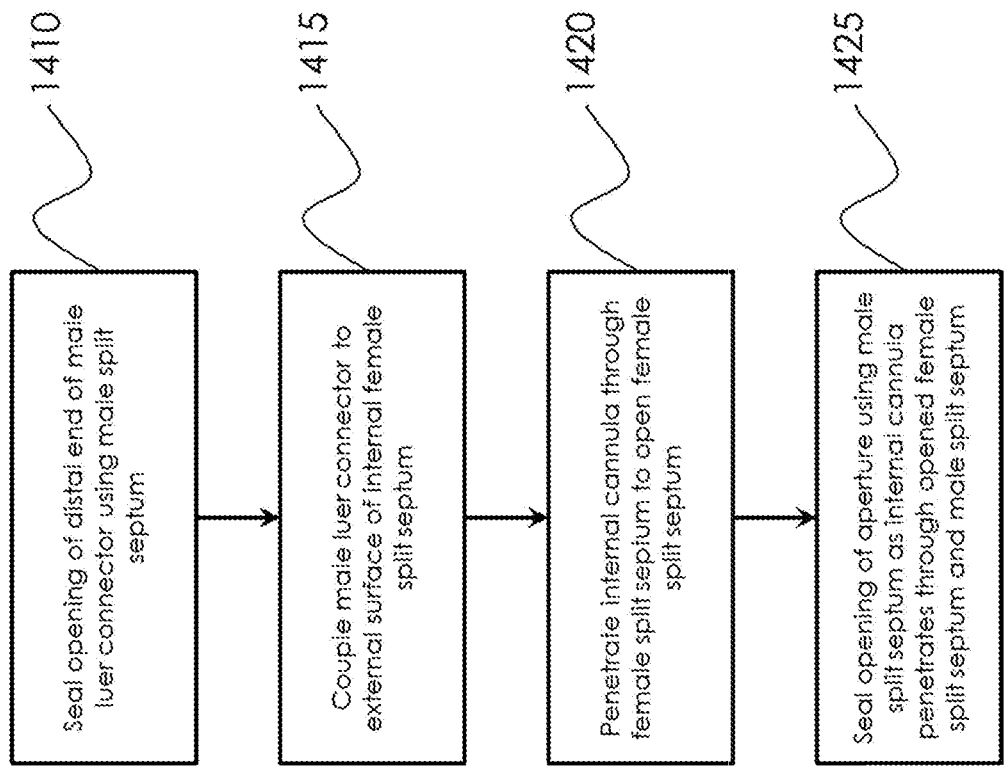
FIG. 14 is a flowchart showing the method of coupling a luer access device according to an exemplary embodiment of the present invention.

In another aspect, FIGS. 14 and 15 illustrate an exemplary process for coupling the luer access device described above according to an exemplary embodiment of the present invention. Referring first to FIG. 14, the process may include sealing an opening of the distal end of the male luer connector using a male split septum (S1410). Then, the male luer connector may be coupled to an external surface of the internal female split septum that is disposed at a proximal end of the female luer connector (S1415). An internal cannula that is disposed in a passageway of the female luer connector may penetrate through the female split septum to open the female split septum (S1420). The male split septum may be used to seal an opening of at least one aperture as the internal cannula penetrates through the opened female split septum and the male split septum (S1425). The aperture may include a plurality of apertures that are disposed through a sidewall of the distal end of the male luer connector. The process may then illustratively end when the female luer connector and the male luer connector are engaged to provide a sterile fluid communication there between.

Referring now to FIG. 15, the process may include coupling the female split septum to an internal wall of the LAD (S1510) and coupling the internal cannula into an end of the female split septum within a passageway of the female luer connector (S1515). The male luer connector may then be coupled to an external surface of the female luer connector (S1520). Further, the female split septum may be opened by the penetration of the internal cannula when coupled with the male luer connector (S1525). As the female splits septum opens, the shape thereof deforms to thus prevent an outer surface from contacting the internal cannula. The process may illustratively end once the female split septum is opened and the internal cannula penetrates into the male luer connector to couple the male luer connector and the female luer connector, providing a sterile fluid communication there between.

As discussed above, the luer access device of the claimed invention is capable of providing a sterile connection between luer connectors, creating a sterile fluid-flow path to safely administer various life-sustaining fluids to patients. The particular design of the split septum in the claimed invention prevents potentially contaminated external surfaces thereof from coming into contact with any sterile surfaces of the fluid-flow path. Accordingly, the LAD of the present invention may be capable of reducing catheter-related bloodstream infections and other contamination-related infections occurring in the related art of needleless connectors.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A luer access device (LAD), comprising:
    a female luer connector having an internal female split septum disposed at a proximal end thereof and coupled to an internal surface of the LAD;
    a male luer connector coupled to an external surface of the internal female split septum;
    a male split septum disposed within a male luer tip and seals an opening of a distal end of the male luer connector; and
    at least one aperture disposed through a sidewall of the distal end of the male luer connector;
    wherein an internal cannula is exposed out of the female luer connector to open the internal female split septum upon engagement with the male luer connector; and
    wherein the male split septum seals an opening of the at least one aperture in the sidewall of the distal end of the male luer connector by penetration of the internal cannula.

2. The LAD of claim 1, wherein the male split septum seals the opening of the at least one aperture in the sidewall of the distal end of the male luer connector when the internal female split septum is opened.

3. The LAD of claim 1, wherein the male split septum is formed as a valve.

4. The LAD of claim 3, wherein a distal end of an inner conduit of the male luer connector forms a seal against a proximal surface of the valve.

5. The LAD of claim 1, wherein the internal female split septum moves down along the internal cannula upon engagement with the male luer connector to expose the internal cannula.

6. The LAD of claim 5, wherein the internal female split septum is moved in response to an elastic force.

7. The LAD of claim 6, wherein the elastic force is output by a resilient member disposed between the internal female split septum and a bottom of the LAD.

8. The LAD of claim 7, wherein the resilient member is a spring or an elastomeric polymer that undergoes elastic deformation upon engagement with the male luer connector.

9. The LAD of claim 1, wherein an interior of the male luer connector is threaded to engage with an external wall of the female luer connector.

10. The LAD of claim 1, wherein the at least one aperture includes a plurality of apertures and wherein the sidewall of the distal end of the male luer connector includes the plurality of apertures.

11. The LAD of claim 10, wherein the plurality of apertures are formed as slots extending from the distal end of the male luer connector.

12. The LAD of claim 1, wherein the internal cannula penetrates into the male luer connector when the internal female split septum is opened to provide fluid communication between the male luer connector and the female luer connector.

13. A method for coupling a luer access device (LAD), comprising:
    sealing an opening of a distal end of a male luer connector using a male split septum;
    coupling the male luer connector to an external surface of an internal female split septum that is disposed at a proximal end of a female luer connector;
    penetrating an internal cannula disposed in a passageway of the female luer connector through the internal female split septum to open the internal female split septum; and
    sealing an opening of at least one aperture using the male split septum as the internal cannula penetrates through the internal female split septum that is opened and the male split septum,
    wherein the at least one aperture is disposed through a sidewall of the distal end of the male luer connector.

14. The method of claim 13, further comprising:
coupling the internal female split septum to an internal wall of the LAD,
wherein the internal female split septum deforms during opening thereof to prevent an outer surface from contacting the internal cannula.

15. The method of claim 13, wherein the internal female split septum is moved down the internal cannula in response to an elastic force output by a resilient member disposed between the internal female split septum and a bottom of the LAD.

16. The method of claim 15, wherein the resilient member is a spring or an elastomeric polymer that undergoes elastic deformation upon coupling of the female luer connector and the male luer connector.

17. The method of claim 13, wherein the male split septum is formed as a valve.

18. The LAD of claim 17, wherein a distal end of an inner conduit of the male luer connector forms a seal against a proximal surface of the valve.

19. The method of claim 13, wherein an interior of the male luer connector is threaded to engage with an external wall of the female luer connector.

20. The method of claim 13, wherein the at least one aperture includes a plurality of apertures and wherein the sidewall of the distal end of the male luer connector includes a plurality of apertures.

21. The method of claim 20, wherein the plurality of apertures are formed as slots extending from the distal end of the male luer connector.

22. The method of claim 13, wherein penetration of the male split septum by the internal cannula and into the male luer connector provides fluid communication between the male luer connector and the female luer connector.

23. The method of claim 14, further comprising:
connecting an external access line to a distal end of the female luer connector and connecting a tube to a proximal end of the male luer connector.

24. A method for coupling a luer access device (LAD), comprising:
coupling a female split septum to an internal wall of the LAD;
coupling an internal cannula into an end of the female split septum within a passageway of a female luer connector;
coupling a male luer connector to an external surface of the female luer connector; and
opening the female split septum by penetration of the internal cannula upon coupling with the male luer connector,
wherein the female split septum deforms during the opening thereof to prevent an outer surface from contacting the internal cannula,
wherein when the female split septum is opened, the internal cannula penetrates into the male luer connector to couple the male luer connector and the female luer connector, and sealing an opening of at least one aperture using the male split septum as the internal cannula penetrates through the female split septum and the male split septum, wherein the at least one aperture is disposed through a sidewall of the distal end of the male luer connector.

25. The method of claim 24, wherein the female split septum moves down along the internal cannula upon engagement with the male luer connector in response to an elastic force.

26. The method of claim 25, wherein the elastic force is output by a resilient member disposed between the female split septum and a bottom of the LAD.

27. The method of claim 26, wherein the resilient member is a spring or an elastomeric polymer that undergoes elastic deformation upon coupling of the female and male luer connectors.

* * * * *